United States Patent
Ishikawa

[11] Patent Number: 5,735,837
[45] Date of Patent: Apr. 7, 1998

[54] URINE-ABSORBENT BAG FOR INCONTINENCE

[75] Inventor: Norihiko Ishikawa, Ehime-ken, Japan

[73] Assignee: Uni-Charm Corporation, Ehime-ken, Japan

[21] Appl. No.: 757,860

[22] Filed: Nov. 27, 1996

[30] Foreign Application Priority Data

Nov. 30, 1995 [JP] Japan ................. 7-312781

[51] Int. Cl.⁶ ................................. A61F 13/15
[52] U.S. Cl. .................. 604/385.1; 604/349; 604/352
[58] Field of Search ................. 604/327–331, 604/349–352, 385.1, 332, 338, 347, 348

[56] References Cited

U.S. PATENT DOCUMENTS

| 4,197,849 | 4/1980 | Bostick. | |
| 4,627,846 | 12/1986 | Ternstrom | 604/349 |
| 4,790,835 | 12/1988 | Elias. | |
| 5,074,853 | 12/1991 | Bryant. | |
| 5,330,454 | 7/1994 | Klinger et al. | 604/338 |
| 5,383,867 | 1/1995 | Klinger. | |

FOREIGN PATENT DOCUMENTS

| 671316 | 10/1963 | Canada | 604/347 |
| 2701389 | 8/1994 | France. | |
| 2708465 | 2/1995 | France. | |

Primary Examiner—Robert A. Clarke
Attorney, Agent, or Firm—Lowe, Price, LeBlanc & Becker

[57] ABSTRACT

A urine-absorbent bag for incontinence having a surrounding wall and an upper peripheral edge defining an opening for insertion of the wearer's penis, the surrounding wall being provided with a cut extending from the upper peripheral edge of the opening toward a bottom edge of the bag so as to divide an upper portion in two, an elastic sheet being attached to the surrounding wall over a region extending in the proximity of the cut.

5 Claims, 3 Drawing Sheets ic of the bag 1, it is also possible to use the liquid-impermeable plastic film alone as the outer sheet 3 without bonding the outer layer 23 thereto.

URINE-ABSORBENT BAG FOR INCONTINENCE

BACKGROUND OF THE INVENTION

The present invention relates generally to a urine-absorbent bag used for male incontinence in bedridden male patients and the like.

A urine-absorbent bag for incontinence and the like is generally formed by a laminate comprising a liquid-permeable topsheet, a liquid-impermeable backsheet and a liquid-absorbent core disposed therebetween. The laminate has an upper peripheral edge thereof defining an opening for insertion of the wearer's penis.

With the known urine-absorbent bag, an adhesive tape or the like is often used to fasten the peripheral edge of the bag opening around the wearer's penis to prevent accidental detachment. However, it is desired that the operation of putting the bag on the wearer's penis should be as simple as possible to unburden nurses or helpers. Particularly, use of the adhesive tape or the like is annoying and most nurses or helpers are reluctant to handle such materials.

SUMMARY OF THE INVENTION

In view of the problem as described above, it is a principal object of the invention to assure that the urine-absorbent bag once put on the wearer's penis cannot be easily detached therefrom.

The object set forth above is achieved, according to the invention. With a urine-absorbent bag for incontinence having a surrounding wall comprising a liquid-permeable topsheet, a liquid-impermeable backsheet and a liquid-absorbent core disposed therebetween, and an upper peripheral edge defining an opening for insertion of the wearer's penis and a bottom edge spaced apart from the opening. The surrounding wall is provided with a cut extending from the upper peripheral edge of the opening toward the bottom edge of the bag to divide an upper portion of the surrounding wall into laterally opposite first and second portions. and An elastic sheet is attached to the surrounding wall over a region extending in the proximity of the cut in order to make the region elastically deformable.

DESCRIPTION OF THE PREFERRED EMBODIMENTS

Figure 1:
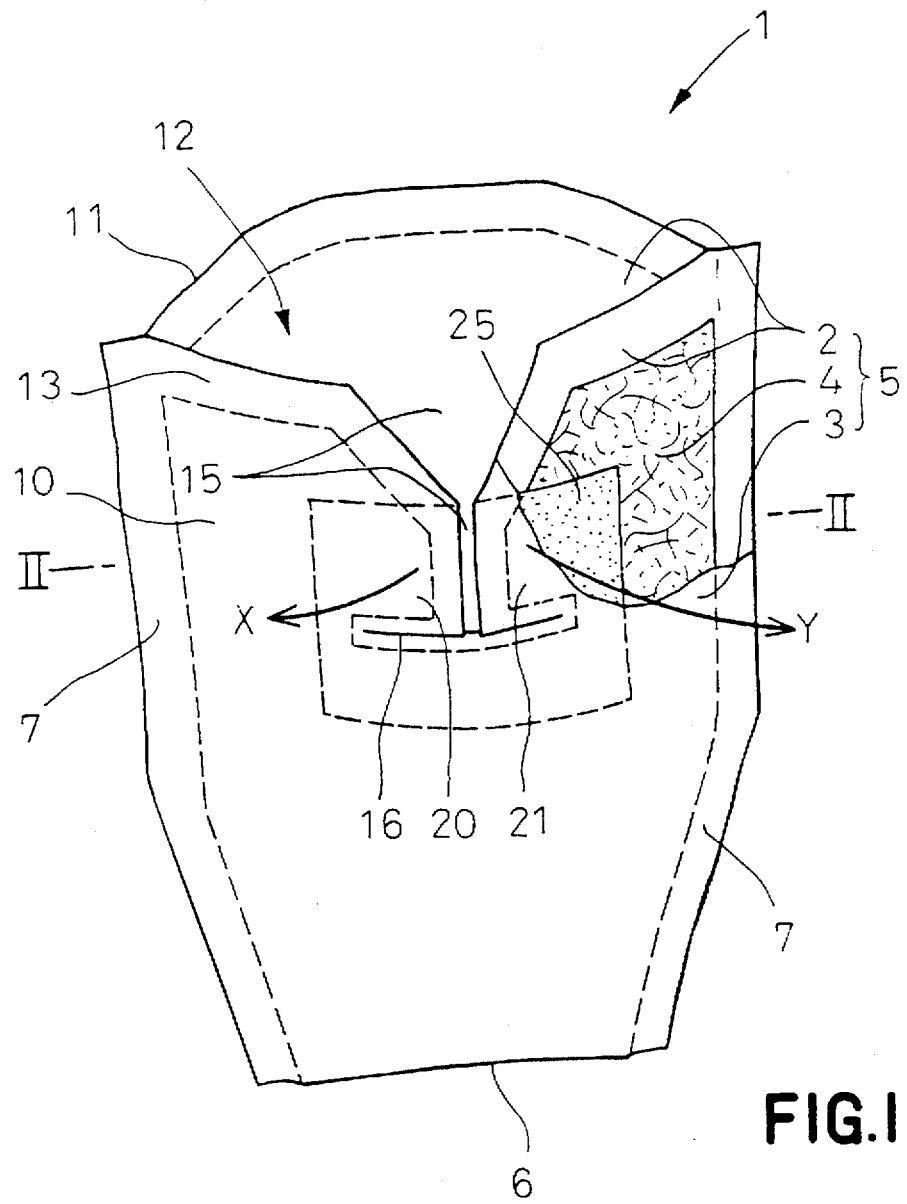
FIG. 1 is a perspective view of an exemplary urine-absorbent bag according to the invention as partially broken away.

A urine-absorbent bag 1 shown by FIG. 1 in a perspective view as partially broken away is made of a laminate 5 comprising a liquid-permeable inner sheet 2, a liquid-impermeable outer sheet 3 and a liquid-absorbent core 4 disposed therebetween. The laminate 5 is folded along a longitudinally middle line 6 with the inner sheet 2 inside and mutually facing marginal regions 7 of respective sections of the folded laminate 5 in two are water-tightly bonded together. More specifically, portions of the inner and outer sheets 2, 3 extending outward beyond a peripheral edge of the core 4 which forms together with the inner and outer sheets 2, 3 the laminate 5 are water-tightly bonded to each other so that the mutually facing portions of the same inner sheet 2 bonded to the outer sheet 3 along the marginal region 7 are bonded together after the laminate 5 has been folded in two, and the longitudinally middle line 9 forms a bottom edge of the bag 1.

The bag 1 comprises a front wall section 10, a rear wall section 11 and an upper opening 12 defined by these two wall sections 10, 11. The front wall section 10 is divided at circumferentially middle region thereof by a first cut 15 extending generally in a Y-shape from the peripheral edge 13 of the opening 12 toward the bottom edge 6 of the bag 1 in a vertical direction in cooperation with a second cut 16 extending from a lower end of the first cut 15 in circumferentially opposite directions so that portions 20, 21 of the front wall section 10 may be folded by a nurse or helper in directions as indicated by arrows X and Y, respectively. As shown, an upper portion of the first cut 15 describes a V-shape toward the edge 13 of the opening 12, but it may also be a U-shape.

Figure 2:
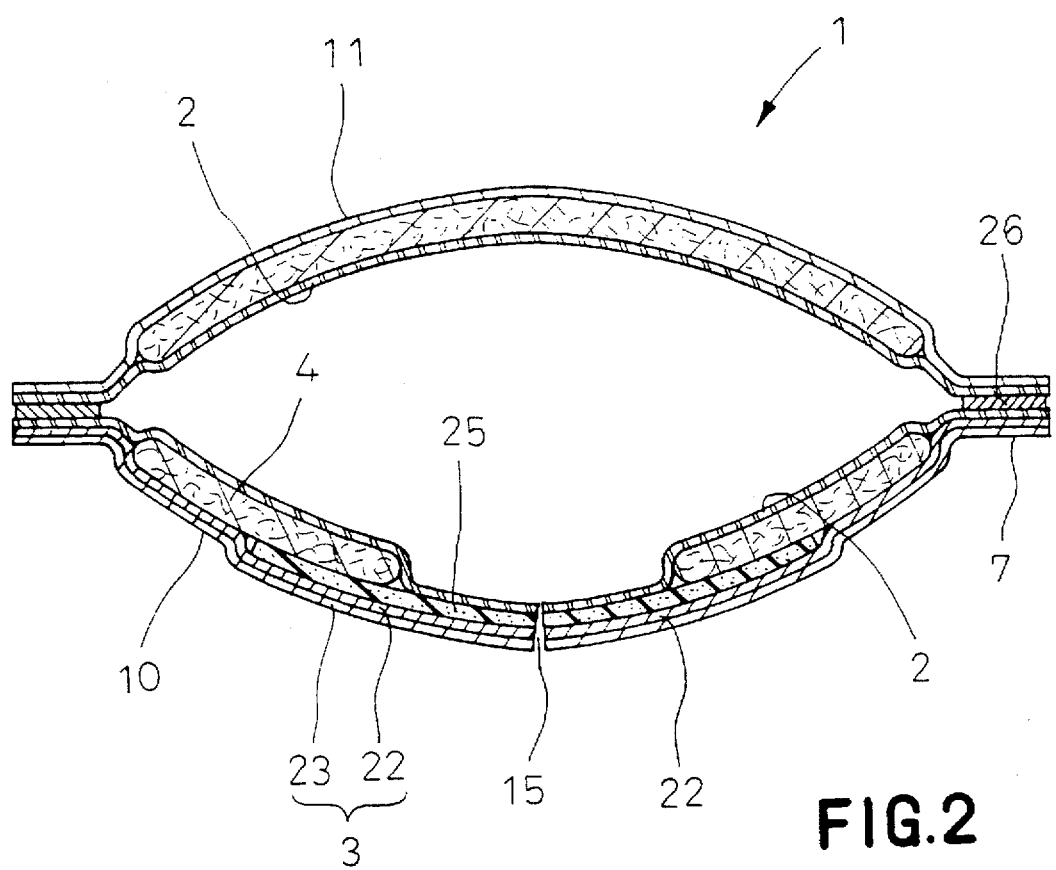
FIG. 2 is a sectional view taken along line II—II in FIG. 1.

FIG. 2 is a sectional view taken along line II—II in FIG. 1, illustrating that the outer sheet 3 of the front wall section 10 comprises an inner layer 22 of liquid-impermeable plastic film and an outer layer 23 of nonwoven fabric. The outer layer 23 is bonded to the inner layer 22 by hot melt type adhesive (not shown). Over a region extending in the proximity of the first and second cuts 15, 16, there is disposed between the inner and outer sheets 2 and 3 a soft and elastic sheet 25 of foamed polyethylene (See FIG. 1 also) which is water-tightly bonded to the inner and outer sheets 2, 3 by hot melt type adhesive (not shown). The front and rear wall sections 10, 11 are bonded to each other by means of hot melt type adhesive 26 along the mutually facing marginal regions 7.

The manner in which the bag 1 is actually used will now be described. The respective portions 20, 21 of the front wall section 10 extending in the proximity of the first and second cuts 15, 16 are folded outward so as to be spaced from each other in the opposite directions X and Y, respectively, and then the forward portion of the wearer's penis is inserted through a space thus provided between the portions 20, 21 into the bag 1. The portions 20, 21 are biased under an elasticity of the soft and elastic sheet 25 to restore their initial positions as soon as a nurse or helper looses her or his hold thereon so as to nip the penis therebetween. Such elasticity of the sheet 25 assures that the bag 1 cannot be easily detached from the wearer's penis during use of the bag 1.

Figure 3:
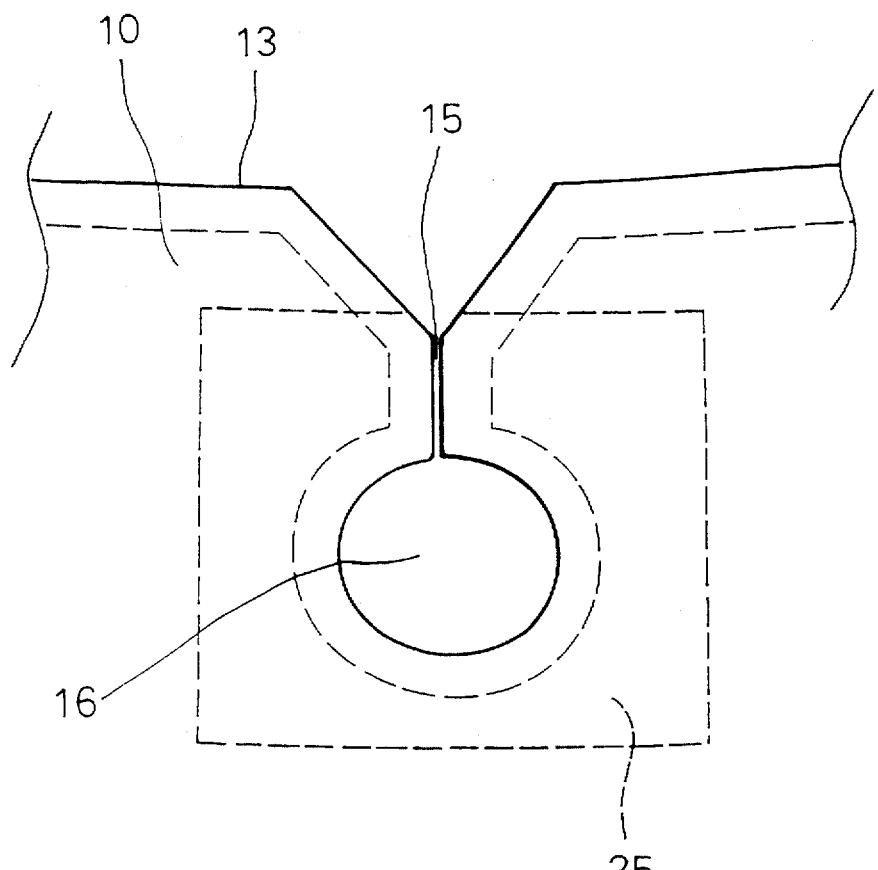
FIG. 3 is a fragmentary diagram illustrating a variant of the inventive urine-absorbent bag.

FIG. 3 is a fragmentary diagram of the front wall section 10 illustrating a possible variant of the bag 1. According to this variant illustrated, the second cut 16 of the first and second cuts 15, 16 cooperating to divide the front wall section 10 substantially in two describes a circle around which the soft and elastic sheet 25 is provided. The bag 1 according to this variant assures more reliably that the bag 1 cannot be easily detached from the wearer's penis, because the second cut 16 is elastically biased by the soft and elastic sheet 25 to fit around the wearer's penis.

Though not shown, the bag 1 may be provided with suitable means for securing the bag 1 to the wearer's undergarment, such as an adhesive tape and a mechanical fastening tape.

For implementation of the invention, liquid-permeable nonwoven fabric is preferably employed as the inner sheet 2. While the outer layer 23 (See FIG. 2) bonded to an outer surface of the outer sheet 3 is effective to improve the touch of a skin-contactable surface of the bag 1, it is obviously possible to implement the invention without use of such outer layer 23. It should be also understood that the soft and elastic sheet 25 may be replaced by any suitable elastic sheet such as rubber sheet, foamed urethane sheet or foamed polystyrene sheet.

The urine-absorbent bag according to the invention is advantageous in that the bag can be reliably held in its operative position, because the elastic wall of the bag always fits around the wearer's penis inserted into the bag.

What is claimed is:

1. A urine-absorbent bag for incontinence comprising a surrounding wall including a liquid-permeable inner sheet, a liquid-impermeable outer sheet and a liquid-absorbent core disposed therebetween, an upper peripheral edge of the surrounding wall defining an opening for insertion of a wearer's penis, and a bottom edge of the wall spaced apart from the opening, wherein:

the surrounding wall is provided with a cut extending from the upper peripheral edge of the opening toward the bottom edge of the bag so as to divide an upper portion of the surrounding wall into laterally opposite first and second portions and a soft elastic sheet is attached to the surrounding wall to extend over and cover the cut in order to enable a region surrounding the cut to be elastically deformable.

2. The urine-absorbent bag according to claim 1, wherein the elastic sheet comprises a foamed plastic or rubber sheet.

3. The urine-absorbent bag according to claim 1, wherein the inner sheet comprises a nonwoven fabric and the outer sheet comprises an inner layer of plastic film and an outer layer of nonwoven fabric.

4. A urine-absorbent bag for incontinence comprising a surrounding wall including a liquid permeable inner sheet, a liquid-impermeable outer sheet and a liquid-absorbent core disposed therebetween, an upper peripheral edge of the surrounding wall defining an opening for insertion of a wearer's penis, and a bottom edge of the wall spaced apart from the opening, wherein:

the surrounding wall is provided with a cut extending from the upper peripheral edge of the opening toward the bottom edge of the bag so as to divide an upper portion of the surrounding wall into laterally opposite first and second portions and a soft elastic sheet is attached to the surrounding wall over a region extending in the proximity of the cut in order to make the region elastically deformable;

wherein the cut comprises a first cut extending generally in a Y-shape from the peripheral edge of the opening toward the bottom edge of the bag and a second cut extending from a lower end of the first cut in circumferentially opposite directions of the bag.

5. A urine-absorbent bag for incontinence comprising a surrounding wall including a liquid permeable inner sheet, a liquid-impermeable outer sheet and a liquid-absorbent core disposed therebetween, an upper peripheral edge of the surrounding wall defining an opening for insertion of a wearer's penis, and a bottom edge of the wall spaced apart from the opening, wherein:

the surrounding wall is provided with a cut extending from the upper peripheral edge of the opening toward the bottom edge of the bag so as to divide an upper portion of the surrounding wall into laterally opposite first and second portions and a soft elastic sheet is attached to the surrounding wall over a region extending in the proximity of the cut in order to make the region elastically deformable;

wherein the cut comprises a first cut extending generally in a Y-shape from the peripheral edge of the opening toward the bottom edge of the bag and a second cut extending from a lower end of the first cut in a circular shape.

* * * * *